(12) United States Patent
Üblacker (10) Patent No.: US 8,491,756 B2
(45) Date of Patent: Jul. 23, 2013

(54) DEVICE FOR DETERMINING THE WATER CONTENT OF A TARGET

(76) Inventor: Dietmar Üblacker, Winklarn (AT)

( * ) Notice: Subject to any disclaimer, the term of this patent is extended or adjusted under 35 U.S.C. 154(b) by 0 days.

(21) Appl. No.: 13/264,566

(22) PCT Filed: Apr. 16, 2010

(86) PCT No.: PCT/AT2010/000113
§ 371 (c)(1),
(2), (4) Date: Oct. 19, 2011

(87) PCT Pub. No.: WO2010/118451
PCT Pub. Date: Oct. 21, 2010

(65) Prior Publication Data
US 2012/0037326 A1    Feb. 16, 2012

(30) Foreign Application Priority Data

Apr. 16, 2009 (AT) .................. A 585/2009
Mar. 12, 2010 (AT) .................. A 404/2010
Mar. 12, 2010 (AT) .................. A 411/2010

(51) Int. Cl.
*D21F 7/06* (2006.01)
(52) U.S. Cl.
USPC ...................................... 162/263
(58) Field of Classification Search
USPC .................. 162/263, 198, 262; 356/445, 430; 250/559.01
See application file for complete search history.

(56) References Cited

U.S. PATENT DOCUMENTS

| | | | |
|---|---|---|---|
| 3,910,701 A | 10/1975 | Henderson et al. | |
| 7,301,164 B2* | 11/2007 | Daugherty et al. | 250/559.01 |
| 7,986,410 B2* | 7/2011 | Bauer et al. | 356/430 |
| 2003/0184746 A1 | 10/2003 | Johnsen et al. | |

FOREIGN PATENT DOCUMENTS

| | | |
|---|---|---|
| DE | 3149869 A1 | 6/1983 |
| EP | 0516913 A2 | 12/1992 |

OTHER PUBLICATIONS

Int'l Search Report issued Sep. 13, 2010 in Int'l Application No. PCT/AT2010/000113.
Office Action and Search Report issued Feb. 14, 2011 in AT Application No. A 404/2010.
Office Action and Search Report issued Feb. 16, 2011 in AT Application No. A 411/2010.

* cited by examiner

*Primary Examiner* — Mark Halpern
(74) *Attorney, Agent, or Firm* — Panitch Schwarze Belisario & Nadel LLP (57) ABSTRACT

A device is provided for determining the water content of a target (1), the device having at least one source of target radiation (2), at least one source of reference radiation (4) directed to a target surface (10), and at least one detecting element (3) for measuring the intensity of radiation reflected back by the target surface. During use the at least one source of target radiation (2), the at least one source of reference radiation (4), and the at least one detecting element (3) are arranged immediately opposite the target surface (10). A pressurizing device using air or gas is provided, by which an artificial movement of the air or gas atmosphere can be created in the area of the optical paths between the at least one source of target radiation (2) and the target surface (10), and/or between the at least one source of reference radiation (4) and the target surface (10), and/or between the target surface (10) and the at least one detecting element (3).

22 Claims, 7 Drawing Sheets

DEVICE FOR DETERMINING THE WATER CONTENT OF A TARGET

CROSS-REFERENCE TO RELATED APPLICATIONS

This application is a Section 371 of International Application No. PCT/AT2010/000113, filed Apr. 16, 2010, which was published in the German language on Oct. 21, 2010, under International Publication No. WO 2010/118451 A1 and the disclosure of which is incorporated herein by reference.

BACKGROUND OF THE INVENTION

The invention relates to a device for determining the water content of a target having at least one source of target radiation and at least one source of reference radiation, both directed to the surface of the target, as well as at least one detecting element for measuring the intensity of the radiation reflected back by the target surface.

Such contactless determination of a water content can be conducted for any target. Such water content determination is particularly but not exclusively required in the manufacture of paper.

In particular, the invention relates to devices for determining the water content of the material mix of water and fibrous materials from which paper is prepared by continuous dehydration.

The water content determination can find use in the exploitation of old fibers or in connection with the process of slurry-pressing from wastewater residues, where the water content of a web of fibrous material mounted on dry sieves is monitored.

According to German published patent application DE 31 49 869 A1, a device for measuring the humidity of a paper web is already known; in the device, two light-emitting diodes emit an alternating pulse frequency of infrared-light pulses with differing wavelengths, and the intensity of the reflected radiation is measured. The wavelength of one of the two light pulses corresponds to the absorbance line in the IR absorbance spectrum of water, while the wavelength of the other light pulse is clearly different from that of the absorbance wavelength and serves as a reference signal. When maintaining the proportion of the intensities of target and reference beams at a constant level, the reflected radiation intensities of both wavelengths are measured, and the water content is determined on that basis. Focusing and reflecting the beam, which is required for measurement, involve a relatively high constructive and technical effort. During operation, device components present in the course of the optical path of the target and reference beams as well as that of the reflected beam are relatively easily contaminated.

In areas of paper manufacturing equipment in which the paper web has a very high water content, the respective environment conditions have not allowed functional measurement so far, as liquid droplets present in the air and other suspended particles result in an immediate blockade of the measurement optics and other optical elements in conventional measurement devices, making operation over an extended period of time impossible.

In other known devices, target and reference beams as well as the reflected radiation are led from and/or to a measurement device through fiber-optic elements. Again, the relatively high technical effort constitutes a disadvantage here, resulting in an increased failure probability and allowing limited measurement sensibility only.

BRIEF SUMMARY OF THE INVENTION

It is thus an object of the invention to provide a device of the above-described kind, which allows water content determination with simple technical means and high accuracy of measurement while requiring minimum service and maintenance.

Another object of the invention is to conduct the contactless water content determination even if the target has a high water content and under rough measurement conditions without diminishing the accuracy or reliability of the measurement.

According to the invention, this is achieved by arranging the at least one source of target radiation, the at least one source of reference radiation, and the at least one detecting element immediately opposite the target surface, and by providing a pressurizing device using air or gas, by which an artificial movement of the air or gas atmosphere can be created in the area of the optical path between the at least one source of target radiation and the target surface, and/or between the at least one source of reference radiation and the target surface, and/or between the target surface and the at least one detecting element.

By the artificial movement of the air or gas atmosphere, contaminants, humidity, germs, or the like are prevented from precipitating on the radiation sources and the detecting element present in the optical path and from interfering with their functionality as time progresses. According to the teachings of the invention, creating locally acting excess pressure prevents contaminants or depositions from interfering with the optical path required for measurement by blocking breakthrough points or passages as well as inlet and outlet openings of radiation sources or detectors, or by covering them with a layer.

Thus, cleaning the device of the invention, which is usually due after a short period of time, is no longer necessary, and the radiation sources and the detecting element can be operated without interconnecting any optical aids such as lenses, mirrors, optical fibers, filters, or protecting glass. This is possible even in very humid and/or dusty environments without compromising the measurement results. Thanks to the artificial movement of the air or gas atmosphere, the device of the invention can be placed in immediate proximity to the target surface to be assessed without worrying about quick contamination of the device. In environments with a risk of explosion, the device of the invention can be used in the danger zone directly without any optical fibers, using suitable inert gases. The facilitation in setting up the device of the invention, which is thus achieved, results in high fail-safety and high sensibility and accuracy of measurement.

A solid set-up of the device of the invention with low dimensions can be achieved when the at least one source of target radiation and the at least one source of reference radiation are each formed by a light-emitting diode. It is also possible, e.g. by a filter, to replace the source of target radiation and the source of reference radiation with a single source of radiation, but in this case, additional constructive measures are required, which may be detrimental to the reliability of the device of the invention.

In order to minimize the number of measurement openings, in further developing the invention, the at least one source of target radiation and the at least one source of reference radiation can be integrated into a shared LED housing. For this purpose, commercial multiple LEDs can be used, in which several pn transitions having different emission wavelengths are present. By using such multiple LEDs, an increase in radiation intensity can also be achieved.

As the source of target radiation and the source of reference radiation are arranged directly opposite the target surface, the radiation reflected by the target area can reach the detecting element without any special aids. It is particularly preferred that the beams emitted by the source of target radiation and the source of reference radiation are uncollimated, which makes it possible that, in orienting the source of target radiation and the source of reference radiation as well as the detecting element, minor deviations from the ideal orientation do not have any significant effect on the measurement results.

Another embodiment of the invention can include the target being a web element, which can be moved relative to the source of target radiation, the source of reference radiation and the detecting element at a constant distance. This applies in particular to the measurement conditions in preparing paper, where the target surface containing water is moved with high speed relative to the device of the invention and the water content is measured while the target is moved.

In order to protect all components of the device of the invention from contamination or other external, such as mechanical, influences, an exemplary embodiment of the invention can provide for the source of target radiation, the source of reference radiation and the detecting element to be arranged in a housing, for which appropriate breakthrough points or passages are formed in a wall of the housing, through which the beams emitted by the source of target radiation and the source of reference radiation exit and through which the beam reflected by the target surface enters.

The radiation produced by the target and the reference sources of radiation is thus allowed to pass through the appropriate breakthrough points or passages and preferably to hit the target surface directly, without any redirection or focusing. The radiation reflected by the surface also passes through a suitable breakthrough point or passage in the housing, arriving at the inlet surface of the detecting element, where it is converted into electrical signals.

Both for reasons of reliability of measurement and for reasons of simplicity of manufacturing it has proven to be advantageous to place the target and the reference sources of radiation as well as the detecting element within the housing in close proximity to each other, whereby the distances covered by the emitted and reflected beams can be kept short and interferences of any kind can be minimized.

However, it is possible that only two breakthrough points or passages are formed, the at least one source of target radiation and the at least one source of reference radiation being integrated within a common LED housing, for which only one of the breakthrough points or passages is disposed.

Thus, another embodiment of the invention can involve the passages in the wall of the housing being formed by through holes in a holder element embedded in the wall, on which those ends of the source of target radiation, the source of reference radiation and the detecting element which are within the housing are arranged, its opposing ends each being directed to the target surface during use.

The beams emitted by the source of target radiation and the source of reference radiation can thereby exit through the respective through holes, while the reflected beam can re-enter through the through holes provided for this purpose.

The central axes of the through holes can be aligned in one plane.

A possible variation of the invention can consist in the central axes of the through holes being arranged in parallel. As the source of target radiation and the source of reference radiation are arranged in close proximity to the detecting element, despite the parallel orientation of the beams, the reflected radiation that arrives at the detecting element will still be sufficiently intense.

In order to increase the intensity of the reflected radiation arriving at the detecting element from the target and reference sources of radiation, according to another variation of the invention, it can be advantageous to have the optical axes of the source of target radiation and the source of reference radiation inclined in such a way that the beams directed to the target surface impinge upon that spot on the target surface which, along a surface normal, is directly opposite the detecting element.

The central axis of the through hole for the detecting element can be oriented normal to the target surface, while the central axes of the through holes for the source of target radiation and the source of reference radiation can enclose an angle for the detecting element with the central axis of the through hole.

It has proven advantageous that the breakthrough points or passages through which the radiation exits or re-enters the housing are designed in such a way that the pressurizing with air or gas against contaminants entering from the outside is conducted immediately in the area of the breakthrough points or passages.

Thus, according to another exemplary embodiment of the invention, the through holes of the holder element can each have at least one side entrance for pressurizing with air or gas. Thereby, a constantly flowing scouring medium stream prevents contaminants or humidity from entering while at the same time it provides the option of cooling or heating the sources of target and reference radiation and the detecting element.

Simple implementation of the side inlets can be provided by forming them by blind holes, which are preferably perpendicular to the central axis of the through holes.

In another embodiment of the invention, the housing can be gas-tight and have a pressure-tight inlet for connecting it to a compressed-air or compressed-gas line. On the one hand, the excess pressure thus created inside the housing by pressurizing prevents contaminants from entering the housing, and on the other hand, it creates an additional air or gas stream from inside the housing through the passages or breakthrough points, which are provided for the target and reference radiation to exit as well as for the radiation reflected by the target surface to enter, whereby constant cleaning of the target and reference sources of radiation and the detecting element occurs provided that clean air or a clean gas is employed.

Another variation of the invention can involve the at least one source of target radiation and the at least one source of reference radiation being arranged on an assumed circle around the at least one detecting element, whereby a beneficial arrangement of multiple sources of radiation can be achieved while measurement can be conducted with the intensity of multiple sources of radiation.

Pressurizing does not have to be done within the housing where the sources of radiation are placed but can be conducted outside of the same. Thus, another embodiment of the invention provides that at the outside of the housing in the area of the breakthrough points or passages a sealing shell is provided, which is in pressure-tight association with the outside of the housing, forms a cavity together with the outside of the housing and has openings which are in line with the breakthrough points or passages, the sealing shell having a pressure-tight inlet for connecting it to the device for pressurizing with air or gas. The sealing shell covers the source of target radiation, the source of reference radiation and the detecting element, which are arranged in the breakthrough points or passages of the housing wall, while at the same it provides the openings for light passing in both directions. During operation, the air or gas under pressure is pressed outside through the sealing shell and the openings therein, thus creating the artificial movement of the air or gas atmosphere that is required for keeping the optical path of the target and reference sources of radiation clear.

The sources of radiation and the detecting element can be protected from contaminants by an interconnected, radiation-transparent element.

According to another exemplary embodiment of the invention, this can be achieved by arranging a radiation-transparent guard plate in each of the optical paths of the at least one source of target radiation and/or of the at least one source of reference radiation and/or of the at least one detecting element.

In order to reduce effects of extraneous light, the radiation-transparent guard plate can be a filter plate which is radiation-transparent in a predefined spectral range only.

Scouring the plate with air or gas can protect it from depositions of particles or droplets present in the surrounding atmosphere; this is done by providing one or more gas or air inlets connected to the pressurizing device, being arranged on that side of the guard plate which is opposite to the at least one source of target radiation, the at least one source of reference radiation, and the detecting element, respectively.

According to another embodiment of the invention, at least one wall opening can be provided in a housing wall which is connected to a tube section protruding outwards, in which the at least one source of target radiation and/or the at least one source of reference radiation and/or the at least one detecting element is/are arranged, and it may be provided that the at least one wall opening is connected to the pressurizing device using air or gas, so that air or gas flows outside via the at least one wall opening and the tube section, thereby scouring the at least one source of target radiation and/or the at least one source of reference radiation and/or the at least one detecting element.

Thus, the air or gas flow is directed from the housing to the outside and thereby flows around the source of radiation arranged inside the tube section or the detector disposed therein.

The sources of radiation and the detector can be disposed in a way that the scouring stream is not directed along the overall length of a tubular cross section but allowed to flow into a tube section at one of its sides.

Thus, another embodiment of the invention can involve the at least one source of target radiation and/or the at least one source of reference radiation and/or the at least one detecting element being disposed in a tubular passage at a certain distance from an opening of the passage which leads outside and the tubular passage being connected to the pressurizing device using air or gas so that air or gas will flow into the area of the optical path of the at least one source of target radiation and/or the at least one source of reference radiation and/or the at least one detecting element.

In order to prevent at least part of the suspended particles present in the air from directly impinging upon the device of the invention, according to another embodiment of the invention, a baffle plate can be provided, the baffle plate covering the area of the sources of radiation and the detector in such a way that particles coming from a particular direction are prevented from impinging upon the area of the optical path, whereby a reduction of radiation intensity due to the deposition of particles on the device of the invention can be avoided.

If the plane in which the baffle plate is arranged is essentially parallel to the optical path of the at least one source of target radiation and/or the at least one source of reference radiation and/or the at least one detecting element, the effect achieved will be particularly good.

Further, it can be provided that the at least one source of target radiation, the at least one source of reference radiation, and the detecting element are arranged within a housing which is attached to the baffle plate on one side. Thereby, the housing may be oriented by mounting it on the baffle plate, which at the same time confers protection against part of the particles that move towards the device of the invention.

Another object of the invention is the detection of the occurrence of a paper web rupture during production in order to avoid idle times and damages to the device. Considering the high conveyor rates and different paper qualities and consistencies, this constitutes quite a substantial problem.

Further, the invention relates to the use of a device of the invention for detecting paper rupture during paper manufacture. The absence of a particular intensity of the reflected radiation signal can be reported to indicate a tear or rupture of the transferred paper web.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
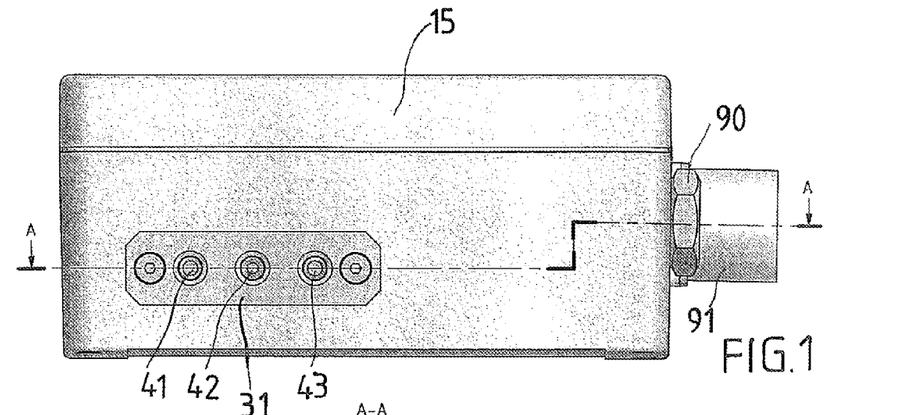
FIG. 1 shows a side view of an embodiment of the device of the invention.
Figure 2:
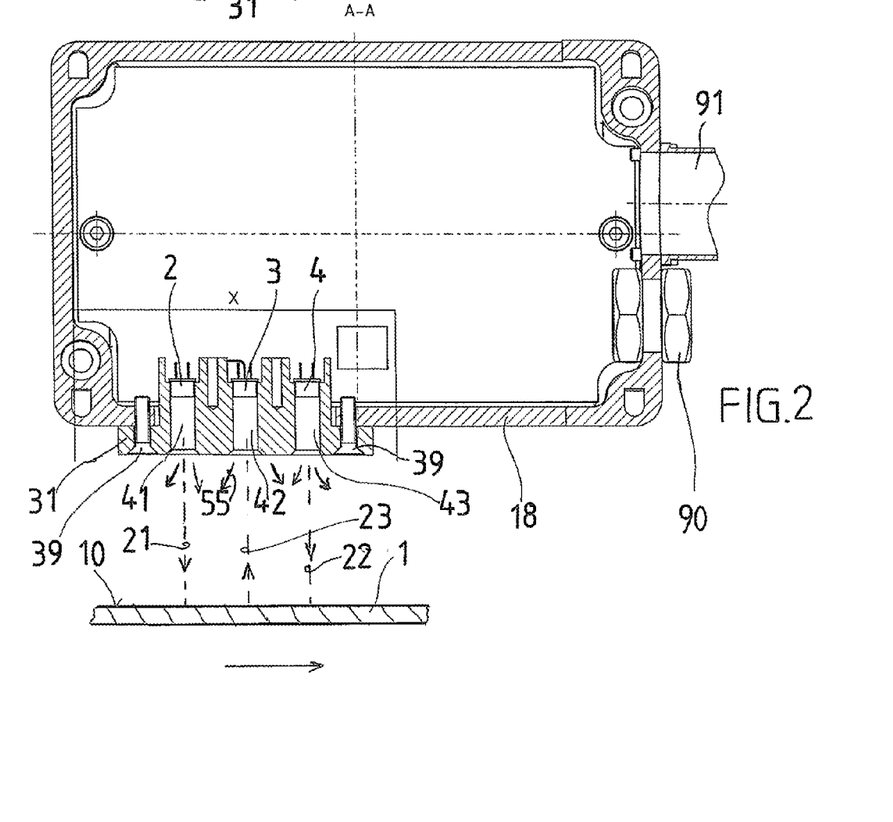
FIG. 2 shows a cross section AA of the embodiment of FIG. 1.

FIGS. 1 and 2 show a device for determining the water content of a target 1, the device being contained in a two-part box-shaped housing 15. For the sake of simplicity, the signal and control units are not depicted. Electrical energy supply and signal or data transfer to a central unit that is not shown occur via a cable connection 90.

A holder element 31, which is fixed with screws 39, is embedded in a gas- and pressure-tight way in a breakthrough point of a wall 18 of the bottom half of the housing 15. In the holder element 31, a source of target radiation 2 and a source of reference radiation 4 are held in such a way that they are directed towards a target surface 10 of the target 1. Further, a detecting element 3 is held by the holder element 31 for measuring the intensity of radiation reflected by the target surface.

According to the invention, the source of target radiation 2, the source of reference radiation 4, and the detecting element 3 are arranged directly opposite the target surface 10 during the measurement procedure. In addition, a pressurizing device using air or gas that is not depicted is provided, the device creating an artificial movement of air or gas atmosphere in the areas of the optical path between the outlet area of the source of target radiation 2 and the target surface 10, between the source of reference radiation 4 and the target surface 10, and between the target surface 10 and the inlet area of the detecting element 3, respectively. This artificial movement of the air or gas atmosphere prevents the source of target radiation 2, the source of reference radiation 4, and the detecting element 3, from being blocked or compromised by contaminants, humidity, or the like.

The source of target radiation 2 and the source of reference radiation 4 are preferably both formed by a light-emitting diode, and the beams emitted by the source of target radiation 2 and the source of reference radiation 4 are uncollimated. The wavelengths emitted by the source of target radiation 2 and the source of reference radiation 4 are in a range from about 1000 nm to 2000 nm. Preferably, the wavelength of the source of target radiation 2 is 1450 nm or 1940 nm, at which the radiation of water is absorbed well, and the wavelength of the source of reference radiation 4 has a value which is clearly different from that of the IR absorbance line, e.g. 1300 nm. The detecting element 3 measures the intensity of the radiation reflected by the target surface 10. The target's water content to be determined is calculated based on the ratio of the intensity at the reference wavelength to that at the target wavelength in relation to calibration runs. The source of target radiation 2 and the source of reference radiation 4 can emit their radiation continuously or in the form of pulses which can be processed accordingly. The advantage of radiation pulses is that of less interference caused by other sources of radiation.

The detecting element 3 is a photo diode or a photo transistor but it can also be formed by a different yet equivalent element.

In the exemplary embodiment shown in FIG. 2, the target 1 is a web element, for example, a paper web, which is moved relative to the source of target radiation, the source of reference radiation, and the detecting element at a constant distance.

Parallel through holes 41, 42 and 43 leading through the wall 18 are recessed in the holder element 31, where at those ends of the through holes that are found within the housing 15, the source of target radiation 2, the detecting element 3, and the source of reference radiation 4 are inserted with their optical axes being oriented along the central axes 21, 22 and 23, while their opposite ends are directed to the target surface 10 during use. For suitable reception of the source of target radiation 2, the detecting element 3, and the source of reference radiation 4, corresponding reception holes 81, 82, 83 are provided at the inner end of the through holes 41, 42 and 43, as shown in detail in FIG. 4 for the exemplary embodiment of FIG. 3.

As seen in FIG. 2, the beams emitted by the source of target radiation 2 and the source of reference radiation 4 along the central axes 21, 22 exiting through the through holes 41, 43 run parallel both to each other and to the beam reflected by the target surface 10 along the central axis 23, which enters through the through hole 42 and is received by the detecting element 3.

In addition, according to FIG. 1, the central axes 21, 23, 22 of the through holes 41, 42, 43 are aligned in the same plane. The type of arrangement and the number of sources of target radiation, sources of reference radiation, and detecting elements used is in no way limited by the scope of the invention.

The lengths of the through holes 41, 42, 43 are preferably about three times their inner diameter, which is provided for a good protection against scattered light sources.

The sources of target and reference radiation 2, 4 and the detecting element 3 can be supported in different ways, for example, only a single passage could be provided for all three elements.

In the exemplary embodiment shown in FIGS. 3 to 6, the source of target radiation 2, the source of reference radiation 4, and the detecting element 3 are oriented in such a way that the beams impinging on the target surface 10 along the central axes 21, 22 meet approximately at one single spot, which is found exactly on the line of a normal to the detecting element 3, i.e. at the spot from where the beam reflected back by the target surface 10 along the central axis 23 enters the detecting element 3.

In order to achieve this, the central axis of the through hole 42 for the detecting element 3 is oriented normal to the target surface 10, and the central axes 21, 22 of the through holes 41, 43 for the source of target radiation 2 and the source of reference radiation 4 enclose an angle α of 7° with the central axis 23 of the through hole 42 for the detecting element 3.

Figure 4:
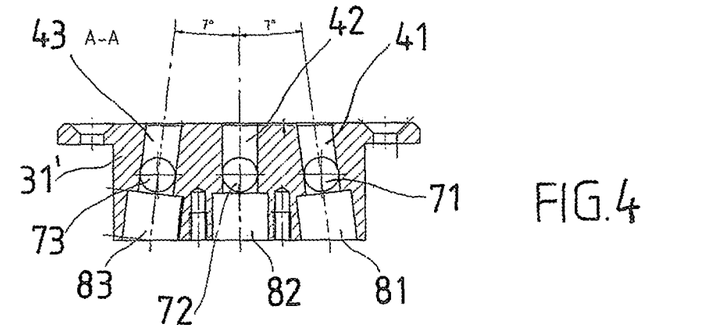
FIG. 4 shows a cross section AA of a holder element of the device shown in FIG. 3.
Figure 5:
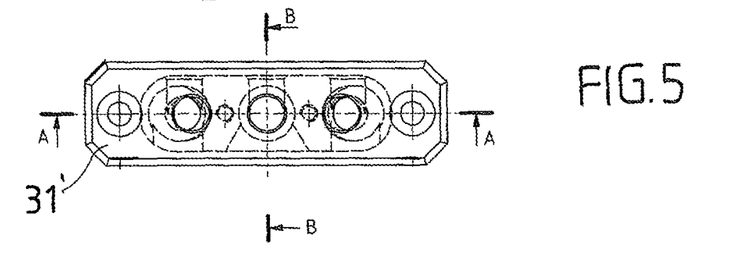
FIG. 5 shows a front view of the holder element shown in FIG. 4.
Figure 6:
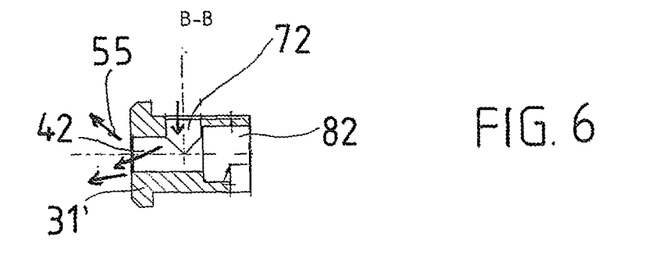
FIG. 6 shows a cross section BB of the holder element shown in FIG. 4.

As shown in FIGS. 4 and 6, the through holes 41, 42, 43 of the holder element 31' each have at least one side inlet 71, 72, 73 for pressurizing using air or gas, each of which is formed by a blind hole which is preferably perpendicular to the central axis of the through holes 41, 42, 43. Although these side inlets are not shown in detail in FIGS. 1 and 2, they are actually present in the device shown therein.

Figure 3:
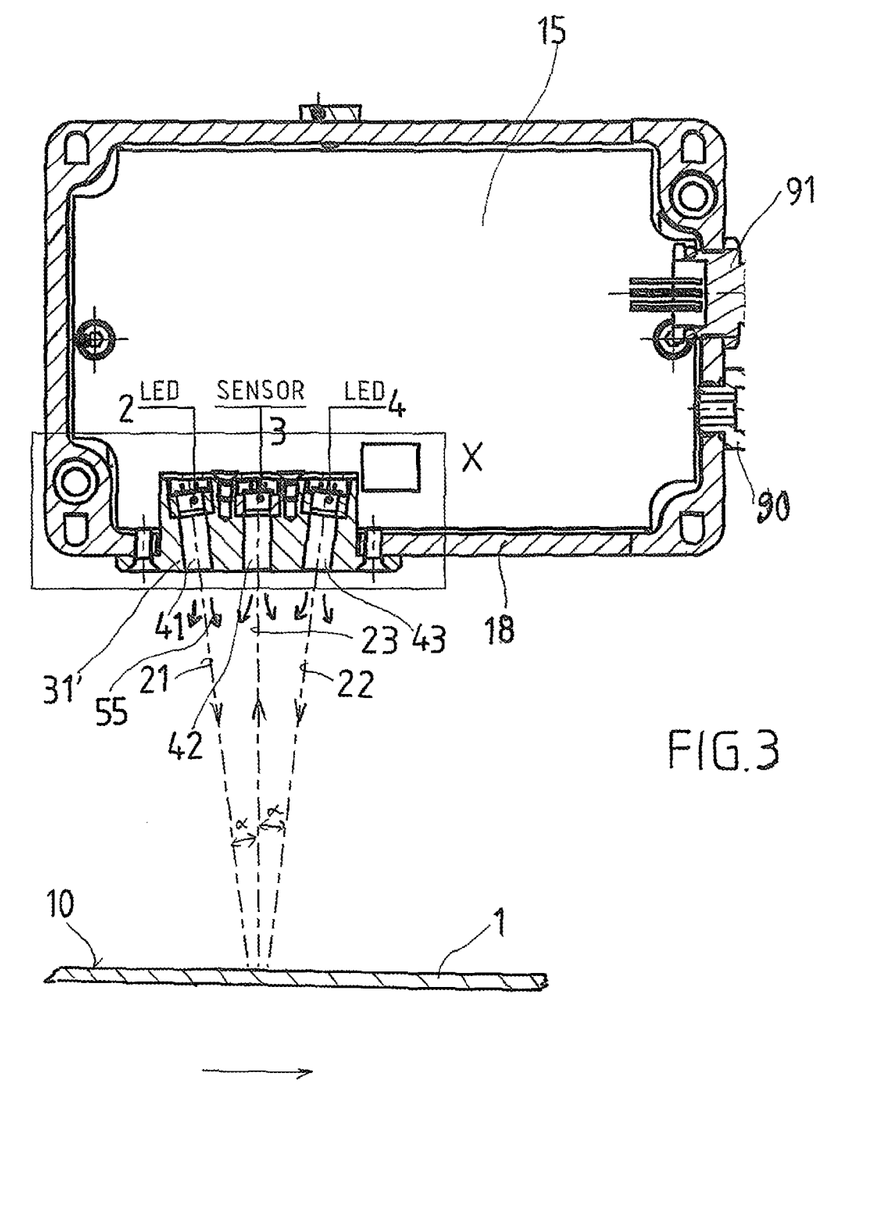
FIG. 3 shows a cross section of another embodiment of the device of the invention.

Pressurizing using air or gas is done by the housing 15 being built gas-tight and having a pressure-tight inlet 91 for connecting it to a compressed-air or compressed-gas line, which represents the pressurizing device. When compressed air is supplied, excess pressure is formed inside the housing 15 compared to the environment, resulting in the escape of the air or gas from inside the housing 15 via the openings required for the beams to pass through and for the optical path to form, and specifically via the side inlets 71, 72, 73 and the three through holes 41, 42, 43, to the outside. The air or gas thus arriving at the outside preferably has high purity, whereby the through holes 41, 42, 43 can be kept clear from contaminants or humidity by the permanent scouring stream. Via temperature regulation of the air or gas flowing in, cooling or heating can be achieved when waste heat is eliminated, or when condensation and/or germination is/are to be avoided.

In environments with a risk of explosion, an inert gas, such as nitrogen or carbon dioxide, can be used as a scouring gas.

Figure 7:
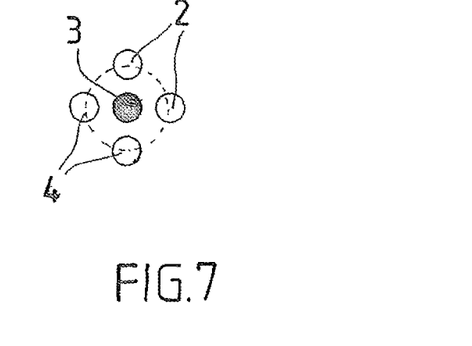
FIG. 7 shows a schematic partial side view of another embodiment of the device of the invention.

FIG. 7 shows another exemplary embodiment, in which, instead of a linear arrangement, two sources of target radiation 2 and two sources of reference radiation 4 are arranged on an assumed circle around the detecting element 3. This arrangement can be varied as desired as far as the number and sequence of the sources of target radiation 2 and the sources of reference radiation 4 are concerned, allowing an increase of the radiation acting on the target 1.

In order to minimize the number of breakthrough points or passages in the housing 15, the source of target radiation 2 and the source of reference radiation 4 can be integrated into a shared LED housing. In this connection, double or triple LEDs have proven particularly advantageous; they have an LED housing with an according number of pn transitions having different wavelengths. A triple LED, for example, can include LEDs having the wavelengths of 1300 nm, 1450 nm, and 1500 nm in a shared LED housing. Thus, for example, it is possible to implement the device of the invention with only two breakthrough points in the housing 15 for the source of target radiation 2, the source of reference radiation 4, and the detecting element 3. In addition, in the case of only two breakthrough points, a smaller amount of air or gas is required for pressurizing. By using multiple LEDs, an increase in radiated intensity can be achieved without the number of breakthrough points being altered as, for example, with three breakthrough points, only two of them may be equipped with multiple LEDs while one is equipped with a detecting element, so that the two multiple LEDs can simultaneously emit the target radiation on the one hand and simultaneously emit the reference radiation on the other hand, whereby a double increase of the emitted intensity can be achieved compared to the arrangement using a single LED.

Figure 8:
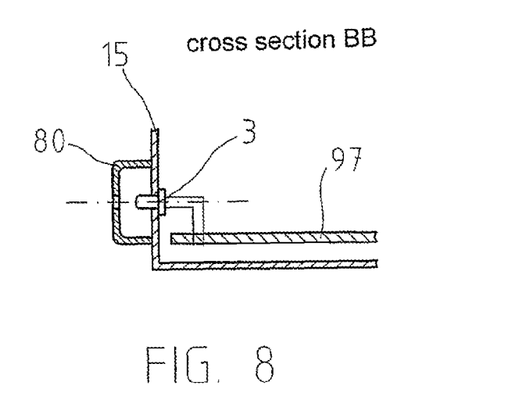
FIG. 8 shows a partial cross section BB of the device of FIG. 9.
Figure 9:
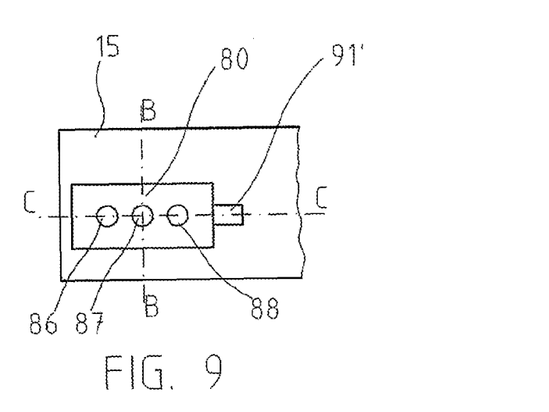
FIG. 9 shows a partial side view of another embodiment of the device of the invention.
Figure 10:
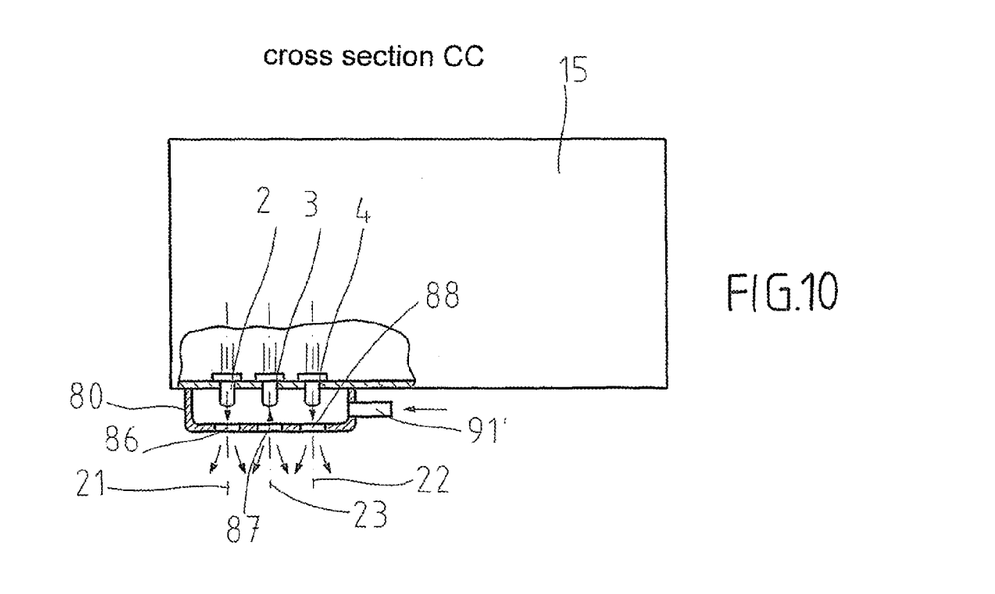
FIG. 10 shows a partial cross section CC of the device of FIG. 9.
Figure 11:
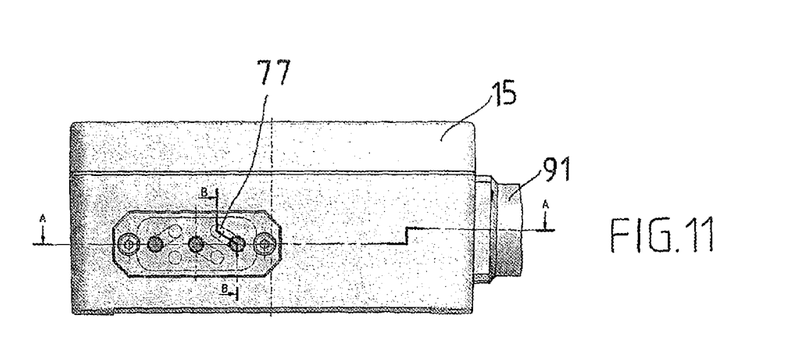
FIG. 11 shows a side view of another embodiment of the device of the invention.

In the exemplary embodiment of FIGS. 8, 9, and 10, at the outside of the housing 15 in the area of the breakthrough points for the sources of target and reference radiation 2, 4 as well as for the detecting element 3, a sealing shell 80 is provided for covering the above, which is connected gas- and pressure-tightly to the outside of the housing 15.

The sealing shell 80 forms a cavity together with the outside of the housing and has openings 86, 87, 88, which are aligned with the breakthrough points, into which the source of target radiation 2, the source of reference radiation 4, and the detecting element 3 are inserted in such a way that their central axes 21, 22 and 23, and respective optical axes are aligned with the openings 86, 87, 88, and the emitted and reflected radiations can both pass through these openings 86, 87, 88 in the sealing shell 80. While the openings 86, 87, 88 have a circular cross-section in the depicted embodiment, they can have any other form, for example, they can be replaced by a single slit of according size.

The source of target radiation 2 and the source of reference radiation 4 are disposed as LEDs, and the detecting element 3 is disposed as a photo diode, all of them arranged on the connection side of a circuit board 97 inside the housing.

The sealing shell 80 has a pressure-tight inlet 91' on its side for connecting it to the pressurizing device using air or gas. During operation, the air or gas exiting from the openings 86, 87 and 88 due to the excess pressure created in the sealing shell 80 keeps the sources of target and reference radiation 2, 4 and the detecting element 3 clear from depositions or contaminants.

Figure 12:
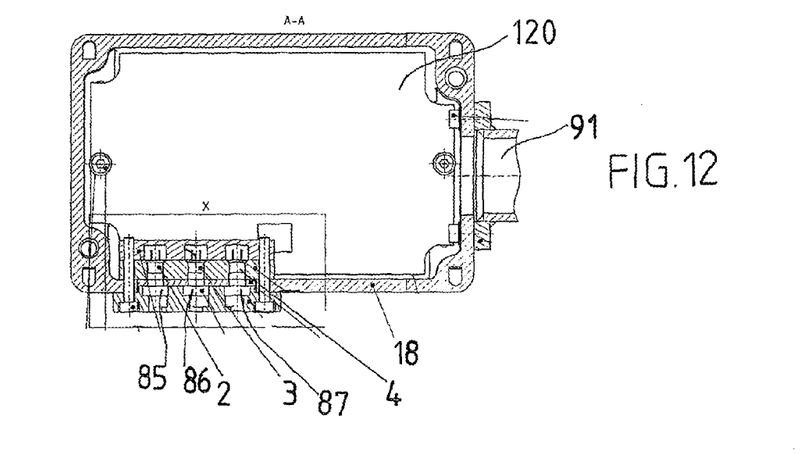
FIG. 12 shows a cross section AA of the embodiment of FIG. 11.

FIGS. 11, 12, 13, and 14 show an exemplary embodiment, in which a radiation-transparent guard plate 85, 86, 87, made from fused quartz, for example, is arranged in each of the source of target radiation 2, the source of reference radiation 4, and the detecting element 3 in order to achieve protection against extraneous mechanical influences while at the same time guaranteeing the free passing of the emitted target and reference radiation as well as the reflected radiation that enters the detecting element 3. FIG. 12 shows a printed circuit board 120 for control units that are not depicted.

However, the radiation-transparent guard plates 85, 86, 87 can also be implemented as filter plates, which are radiation-transparent in predefined spectral ranges only, in order to reduce the effects of extraneous light.

Figure 13:
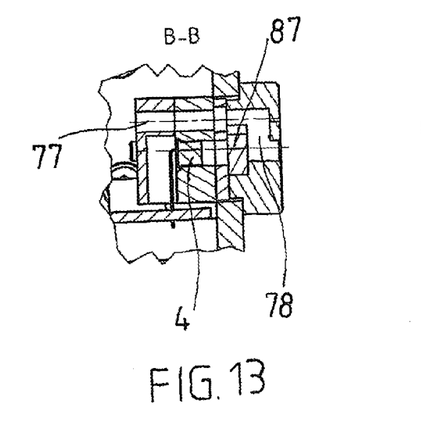
FIG. 13 shows a cross section BB of a detail of the embodiment of FIG. 11.
Figure 14:
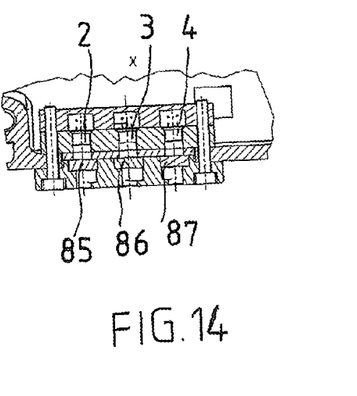
FIG. 14 shows a detail of FIG. 12.

FIG. 13 is a detailed representation of a gas or air vent 77, which is connected to the device for pressurizing using air or gas at one of its ends and forms a gas or air inlet 78 at its other end, which is disposed on the side of the guard plate 87 opposite the source of reference radiation 4 and leads sideways into the through hole that leads outside and receives the source of radiation 4 at its end inside the housing. Accordingly, other gas or air inlets for the source of target radiation 2 and the detecting element 3 are provided yet not illustrated. Thus, scouring with gas or air occurs on that side of the guard plates 85, 86, 87 which is turned away form the sources of radiation 2, 4 and the detector 3.

Figure 15:
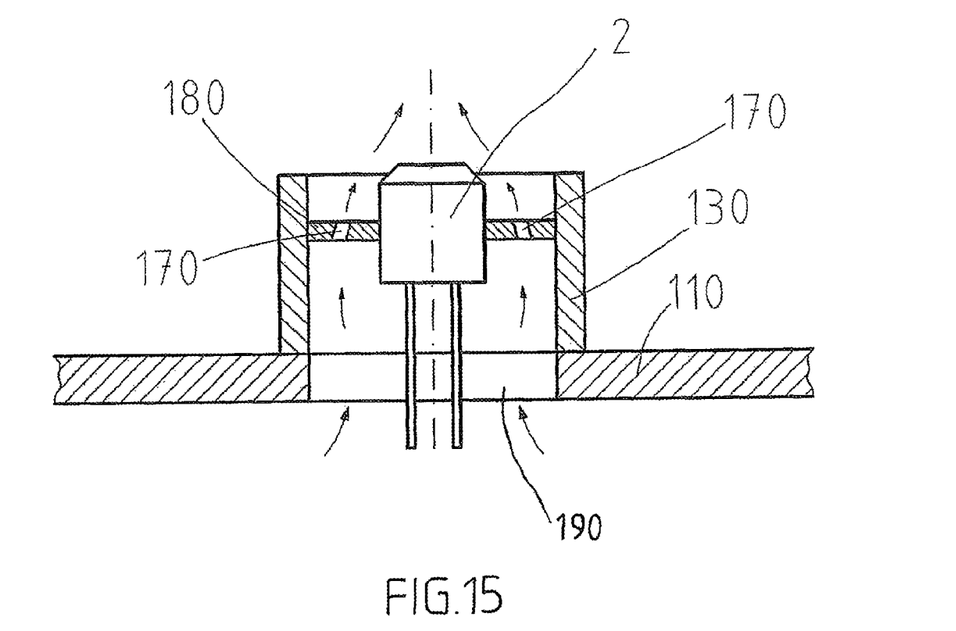
FIG. 15 shows a cross section of a detail of another embodiment of the device of the invention.

FIG. 15 shows a detail of another exemplary embodiment, in which a wall opening 190 is disposed in a housing wall 110 which is connected to a tube section 130 that protrudes outwards.

Inside the tube section 130, the source of target radiation 2 is disposed, which is held by a retaining disc 180 with holes 170. The wall opening 190 is connected to the pressurizing device, for example, via a housing cavity, which is not depicted, so that air or gas flows outside through the wall opening 190 (indicated by arrows), the tube section 130, and the holes 170, thus scouring the source of target radiation 2. Accordingly, this arrangement can be used for the source of reference radiation and the detecting element as well.

Figure 16:
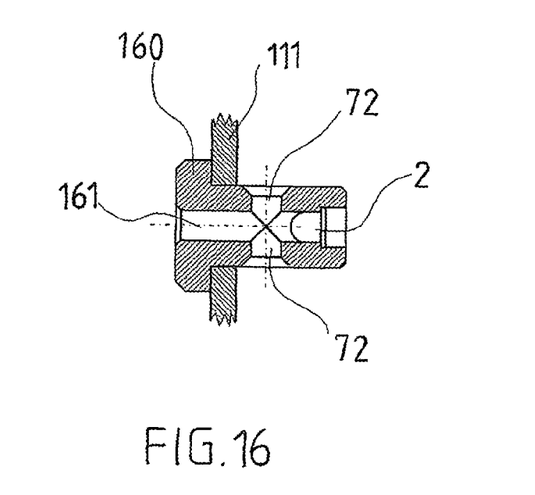
FIG. 16 shows a cross section of a detail of another embodiment of the device of the invention.

Another exemplary embodiment of the invention is shown in detail in FIG. 16, in which the source of target radiation 2 is arranged in a tubular passage 160 at a certain distance from an opening 161 of the passage 160 that leads outside. The tubular passage 160 is connected to the pressurizing device using air or gas via side inlets 72, so that air or gas flows in the area of the optical path of the source of target radiation 2. The source of reference radiation or the detecting element can be disposed in the place of the source of target radiation 2.

Figure 17:
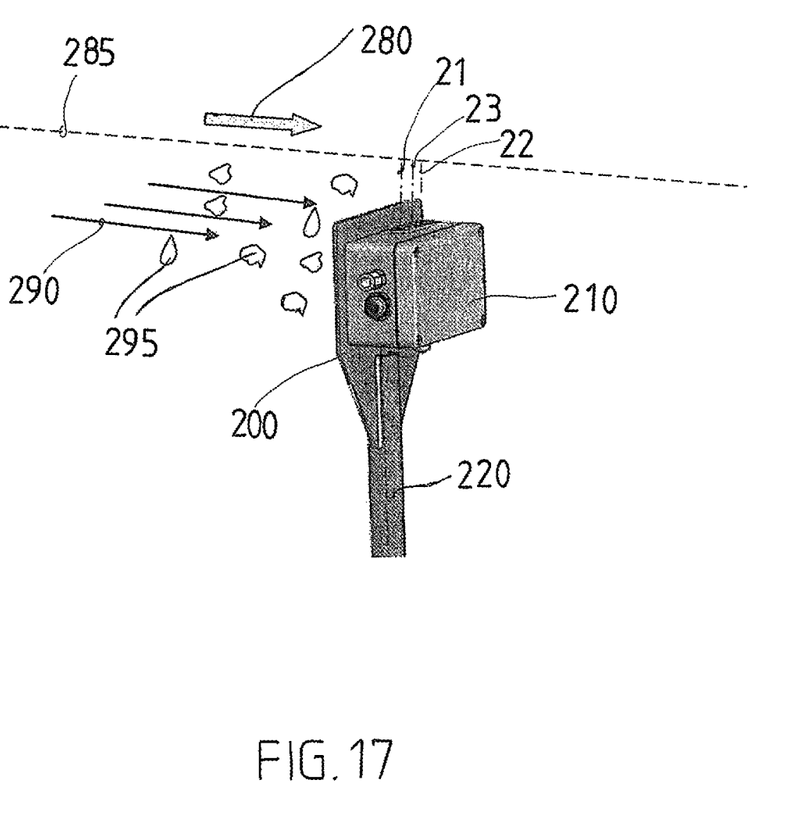
FIG. 17 shows an oblique projection of a mounting arrangement of an embodiment of the invention.

FIG. 17 shows an arrangement of a device of the invention disposed in a housing 210 in the area of a paper manufacturing device for which the paper web being manufactured is indicated by a dotted line 285 moving in the direction indicated by the arrow 280. For protection against direct influence of suspended particles 295 generated during production, a baffle plate 200 covering one side of the housing is disposed, which is kept in a position at right angles to the propagation direction of the suspended particles 295.

The plane of the baffle plate 200 is essentially parallel to the optical path of the beams 21, 22, 23, which exit from the sources of target and reference radiation and enter into the detecting element, mounted inside the housing 210. The housing 210 is mounted on the baffle plate 200 at one of its sides.

The device of the invention can find use in detecting paper rupture during paper manufacturing, by detecting the sudden absence of absorbance of radiation emitted by the source of target radiation and impinging upon the paper web in the detecting element.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device for determining the water content of a target (1), the device comprising at least one source of target radiation (2), at least one source of reference radiation (4) oriented toward a target surface (10), and at least one detecting element (3) for measuring the intensity of radiation reflected back by the target surface, the at least one source of target radiation (2), the at least one source of reference radiation (4), and the at least one detecting element (3) being arranged immediately opposite the target surface (10) during use, and a pressurizing device using a gas by which an artificial movement of a gas atmosphere is created in an area of optical paths between the at least one source of target radiation (2) and the target surface (10) and/or between the at least one source of reference radiation (4) and the target surface (10) and/or between the target surface (10) and the at least one detecting element (3);
- wherein the source of target radiation (2), the source of reference radiation (4), and the detecting element (3) are arranged in a housing (15), in which corresponding passages are formed in a wall (18) of the housing (15), through which passages beams emitted by the source of target radiation (2) and the source of reference radiation (4) exit and a beam reflected by the target surface (10) enters;
- wherein the passages in the wall (18) of the housing (15) are formed as through holes (41, 42, 43) in a holder element (31, 31'), at the ends of which inside the housing (15) the source of target radiation (2), the source of reference radiation (4), and the detecting element (3) are arranged, while their opposite ends are directed towards the target surface (10) during use;
- wherein optical axes of the source of target radiation (2), the source of reference radiation (4), and the detecting element (3) are oriented along central axes (21, 22, 23) of the through-holes (41, 42, 43);
- wherein the through holes (41, 42, 43) of the holder element (31, 31') each have at least one side inlet (71, 72, 73) connected to the pressurizing device and oriented perpendicularly with respect to the central axes (21, 22, 23) through which the gas is introduced into the through holes (41, 42, 43); and
- wherein a diameter of the through-holes (41, 42, 43) and a diameter of the at least one side inlet (71, 72, 73) are approximately equal.

2. The device according to claim 1, wherein the at least one source of target radiation (2) and the at least one source of reference radiation (4) each comprise a light-emitting diode.

3. The device according to claim 1, wherein the at least one source of target radiation (2) and the at least one source of reference radiation (4) are integrated into a shared LED housing.

4. The device according to claim 1, wherein the beams emitted by the at least one source of target radiation (2) and the at least one source of reference radiation (4) are uncollimated.

5. The device according to claim 1, wherein the target (1) is a web element movable relative to the source of target radiation (2), the source of reference radiation (4), and the detecting element (3) at a constant distance.

6. The device according to claim 1, wherein only two passages are formed and wherein the at least one source of target radiation (2) and the at least one source of reference radiation (4) are integrated into a shared LED housing, for which only one of the passages is provided.

7. The device according to claim 1, wherein the holder element (31, 31') is embedded in the wall (18).

8. The device according to claim 1, wherein the central axes of the through holes (41, 42, 43) are aligned in a same plane.

9. The device according to claim 8, wherein the central axis of the through hole (42) for the detecting element (3) is oriented normal to the target surface (10), and wherein the central axes of the through holes (41, 43) for the source of target radiation (2) and the source of reference radiation (4), respectively, each enclose an angle α with the central axis of the through hole (42) for the detecting element (3).

10. The device according to claim 8, wherein the central axes of the through holes (41, 42, 43) are arranged in parallel.

11. The device according to claim 1, wherein the side inlets (71, 72, 73) comprise blind holes.

12. The device according to claim 1, wherein the at least one source of target radiation (2) and the at least one source of reference radiation (4) are arranged on an assumed circle around the at least one detecting element (3).

13. The device according to claim 1, wherein the housing (15) is formed gas-tight and has a pressure-tight inlet (91) for connecting the housing to the pressurizing device.

14. The device according to claim 1, further comprising a sealing shell (80) disposed on an outside of the housing (15) in an area of the passages for covering the passages, wherein the sealing shell is connected pressure-tightly to the outside of the housing (15), forms a cavity together with an outer wall of the housing, has openings (81, 82, 83) aligned with the passages, and has a pressure-tight inlet (91') for connection to the pressurizing device.

15. The device according to claim 1, further comprising a radiation-transparent guard plate (85, 86, 87) arranged in the optical paths of each of the at least one source of target radiation (2) and/or the at least one source of reference radiation (4) and/or the at least one detecting element (3).

16. The device according to claim 15, wherein the radiation-transparent guard plate comprises a filter plate that is radiation-transparent only within a predefined spectral range.

17. The device according to claim 15, further comprising one or more gas inlets (78) connected with the pressurizing device using gas and arranged on a side of the guard plate (85, 86, 87) opposite to the at least one source of target radiation (2), the at least one source of reference radiation (4), and the detecting element (3), respectively.

18. The device according to claim 1, further comprising at least one wall opening (190) in a housing wall (110), the wall opening being connected to a tube section (130) protruding outwards, in which the at least one source of target radiation (2) and/or the at least one source of reference radiation (4) and/or the at least one detecting element (3) is/are arranged, wherein the at least one wall opening (190) is connected to the pressurizing device using gas, such that gas flows outside through the at least one wall opening (190) and the tube section (130) to scour the at least one source of target radiation (2) and/or the at least one source of reference radiation (4), and/or the at least one detecting element (3).

19. The device according to claim 1, wherein the at least one source of target radiation (2) and/or the at least one source of reference radiation (4) and/or the at least one detecting element (3) is/are arranged in a tubular passage (160) at a certain distance from an opening of the passage (160) that leads outside, and wherein the tubular passage (160) is connected to the pressurizing device using gas, such that the gas flows in an area of the at least one source of target radiation (2)

and/or the at least one source of reference radiation and/or the at least one detecting element.

20. The device according to claim 1, further comprising a baffle plate (200).

21. The device according to claim 20, wherein a plane of the baffle plate (200) is essentially parallel to the optical path of the at least one source of target radiation (2) and/or the at least one source of reference radiation and/or the at least one detecting element.

22. The device according to claim 20, wherein the at least one source of target radiation and the at least one source of reference radiation and the at least one detecting element are arranged within a housing (210) mounted on the baffle plate (200) at one of its sides.

* * * * *